United States Patent
Ariyoshi

(10) Patent No.: US 8,996,317 B2
(45) Date of Patent: Mar. 31, 2015

(54) SAMPLE ANALYZER, COMPUTER PROGRAM PRODUCT FOR A SAMPLE ANALYZER AND METHOD FOR ANALYZING A SAMPLE

(75) Inventor: Shunsuke Ariyoshi, Kobe (JP)

(73) Assignee: Sysmex Corporation, Kobe-shi, Hyogo (JP)

( * ) Notice: Subject to any disclaimer, the term of this patent is extended or adjusted under 35 U.S.C. 154(b) by 1001 days.

(21) Appl. No.: 12/868,405

(22) Filed: Aug. 25, 2010

(65) Prior Publication Data

US 2011/0054847 A1    Mar. 3, 2011

(30) Foreign Application Priority Data

Aug. 25, 2009  (JP) ................. 2009-194745

(51) Int. Cl.
*G01N 35/00* (2006.01)
*G01N 15/12* (2006.01)
*G01N 15/14* (2006.01)

(52) U.S. Cl.
CPC ...... *G01N 35/00693* (2013.01); *G01N 15/1209* (2013.01); *G01N 15/1429* (2013.01)
USPC ......................................... 702/19

(58) Field of Classification Search
USPC ............. 702/19, 22, 23, 85, 183; 436/73, 155
See application file for complete search history.

(56) References Cited

U.S. PATENT DOCUMENTS

| | | | |
|---|---|---|---|
| 7,318,336 B2 | 1/2008 | Roth et al. | |
| 7,580,120 B2 | 8/2009 | Hamada et al. | |
| 2005/0164375 A1 | 7/2005 | Inoue | |
| 2006/0073606 A1* | 4/2006 | Fukuda | 436/155 |

FOREIGN PATENT DOCUMENTS

CN           101460827 A     6/2009

* cited by examiner

*Primary Examiner* — Mohamed Charioui
(74) *Attorney, Agent, or Firm* — Brinks Gilson & Lione

(57) ABSTRACT

A sample analyzer comprising: a measuring unit, which comprises a signal output section for outputting a signal representing a characteristic of a measurement specimen prepared by mixing a sample with a reagent, and a signal adjusting section for adjusting the signal outputted from the signal output section, the measuring unit outputting a detection signal based on the signal adjusted by the signal adjusting section; and a result producing unit for producing an analysis result based on the detection signal outputted from the measuring unit and storing the analysis result therein is disclosed. A computer program product for the sample analyzer and a method for analyzing a sample using such a sample analyzer is also disclosed.

15 Claims, 14 Drawing Sheets

*FIG. 4*

| SAMPLE ID | LYMPH-X | NEUT-Y | ⋯ ⋯ ⋯ | MEASUREMENT DATE |
|---|---|---|---|---|
| XXXX | XXXX | XXXX | ⋯ ⋯ ⋯ | XX/XX/XX |
| XXXX | XXXX | XXXX | ⋯ ⋯ ⋯ | XX/XX/XX |
| ⋮ | ⋮ | ⋮ | ⋮ | ⋮ |
| ⋮ | ⋮ | ⋮ | ⋮ | ⋮ |
| ⋮ | ⋮ | ⋮ | ⋮ | ⋮ |

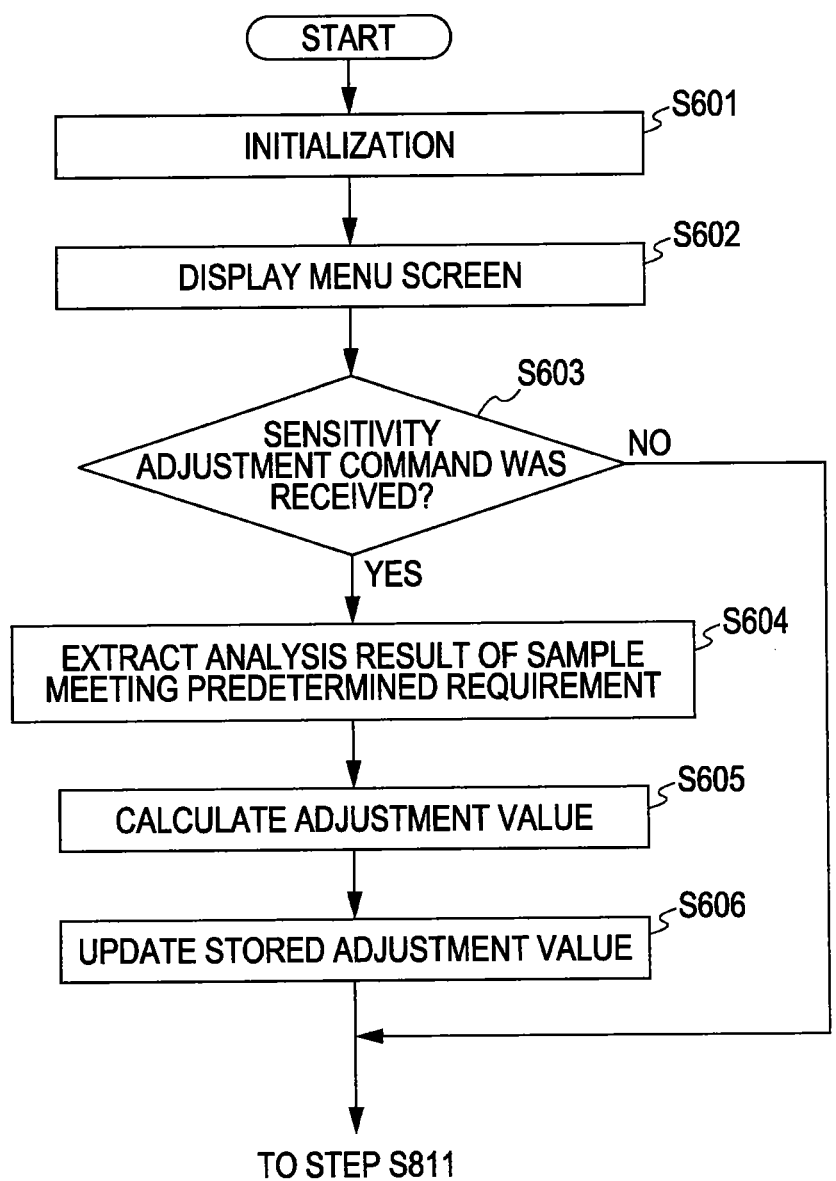

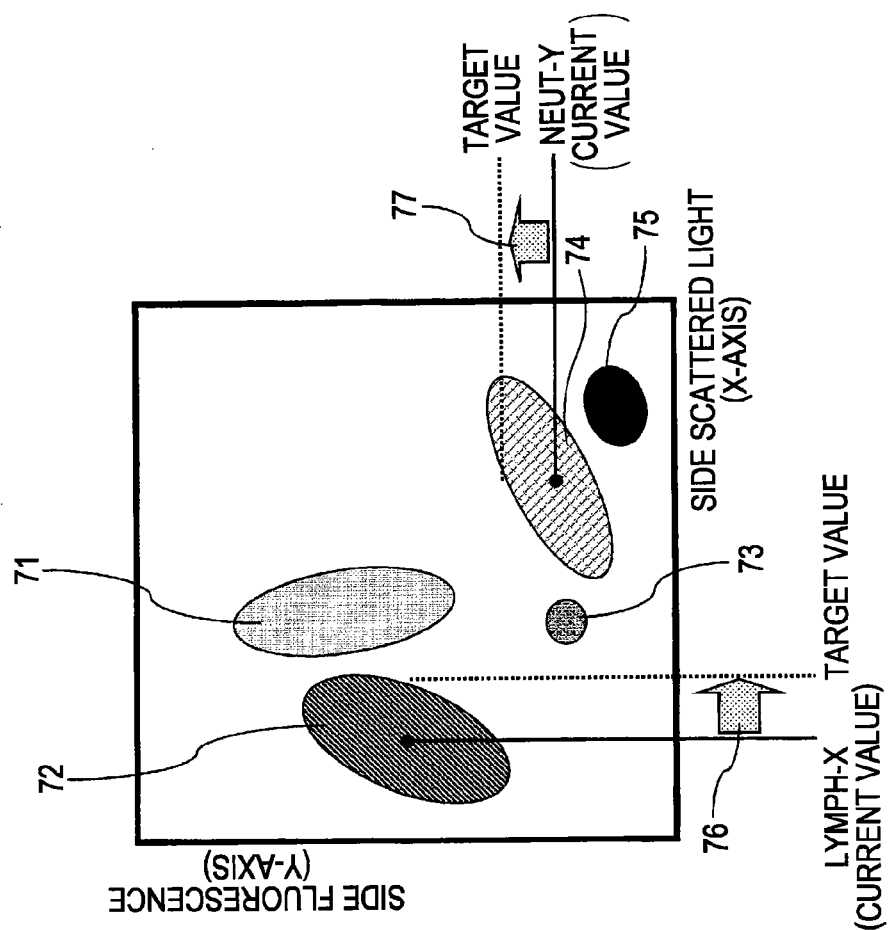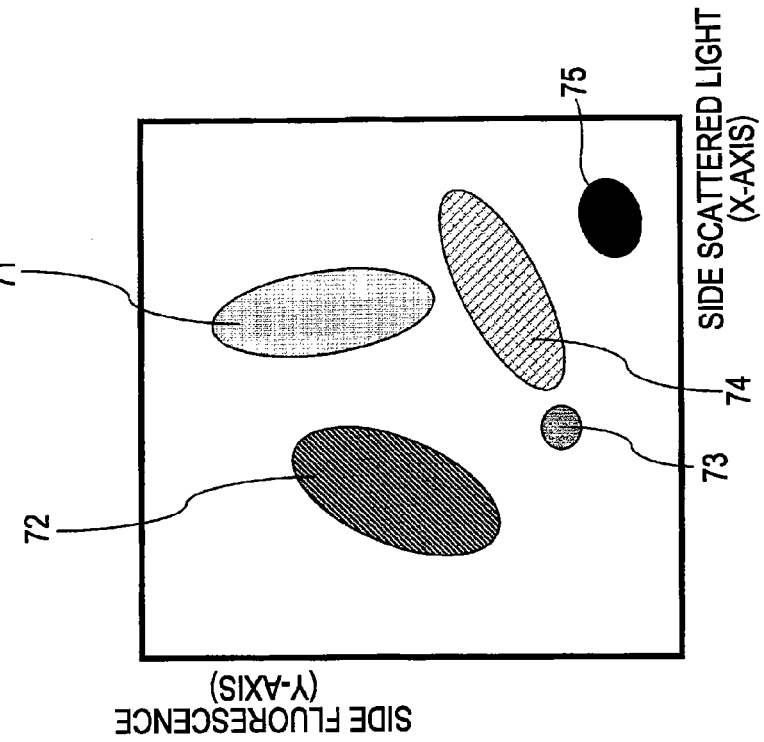

FIG. 11

| SAMPLE ID | HGB | MCV | WBC | PLT | LYMPH-X | NEUT-Y | ...... | MEASUREMENT DATE |
|---|---|---|---|---|---|---|---|---|
| xxxx | xxxx | xxxx | xxxx | xxxx | xxxx | xxxx | ...... | xx/xx/xx |
| xxxx | xxxx | xxxx | xxxx | xxxx | xxxx | xxxx | ...... | xx/xx/xx |
| ... | ... | ... | ... | ... | ... | ... | ... | ... |

US 8,996,317 B2

SAMPLE ANALYZER, COMPUTER PROGRAM PRODUCT FOR A SAMPLE ANALYZER AND METHOD FOR ANALYZING A SAMPLE

RELATED APPLICATIONS

This application claims priority under 35 U.S.C. §119 to Japanese Patent Application No. 2009-194745 filed on Aug. 25, 2009, the entire content of which is hereby incorporated by reference.

FIELD OF THE INVENTION

The present invention relates to a sample analyzer for analyzing components included in a sample such as blood or urine by performing measurement to the sample, a computer program for such a sample analyzer and method for analyzing a sample.

BACKGROUND OF THE INVENTION

Conventionally, a wide variety of sample analyzers for analyzing cell components included in a sample such as blood or urine have been developed. For example, U.S. Pat. No. 7,580,120 discloses a blood analyzer for counting cell components of blood after sorting the components into different groups such as red blood cells, white blood cells, and platelets. According to the blood analyzer, a measurement specimen prepared by mixing a blood sample with a reagent suitable for a particular measurement item is poured into a flow cell, and a liquid flow in the flow cell is irradiated with light from a light source, so that light generated by the irradiation of the light is received by a light receiving element. Then, the received light is photo-electrically converted to obtain an electrical signal, and the blood component can be analyzed by observing variation of the obtained electrical signal.

Apart from the above-mentioned analyzer which optically analyzes the sample, there is a sample analyzer which utilizes an electrical resistance, wherein cell components of a sample such as blood or urine are analyzed by observing variation of the electrical resistance. In either of the analyzers, an analysis result thereby obtained is largely affected by a sensitivity of a sensor, such as light receiving element or resistance sensor (current sensor).

To suitably retain the sensitivity of the sensor, sensors of the conventional sample analyzers are needed to be periodically adjusted. To adjust the sensitivity, an analysis result obtained by actually analyzing a sample obtained from a patient is used. The sensitivity is adjusted so that an analysis result of a sample, which is very likely to demonstrate a particular result, falls within a predetermined range.

In the conventional sample analyzer disclosed in U.S. Pat. No. 7,580,120, it is necessary to stock a plurality of samples whose analysis results fall within a predetermined range, that is, a plurality of samples having a homogeneous characteristic. However, most of the samples such as blood and urine are, in fact, not homogenous, and it imposes an excessive load on a user of the analyzer to search analysis results of any suitable samples in a huge volume of analysis results.

SUMMARY OF THE INVENTION

The scope of the invention is defined solely by the appended claims, and is not affected to any degree by the statements within this summary.

A first aspect of the presented invention is a sample analyzer comprising: a measuring unit, which comprises a signal output section for outputting a signal representing a characteristic of a measurement specimen prepared by mixing a sample with a reagent, and a signal adjusting section for adjusting the signal outputted from the signal output section, the measuring unit outputting a detection signal based on the signal adjusted by the signal adjusting section; and a result producing unit for producing an analysis result based on the detection signal outputted from the measuring unit and storing the analysis result therein, wherein the result producing unit: extracts an analysis result of a sample meeting a predetermined requirement from a plurality of analysis results stored therein; calculates an adjustment value which is to be used in the signal adjustment by the signal adjusting section based on the extracted analysis result; and transmits the calculated adjustment value to the measuring unit, and the signal adjusting section adjusts the signal outputted from the signal output section based on the received adjustment value.

A second aspect of the presented invention is a computer program product for a sample analyzer, the sample analyzer comprising: a measuring unit, which comprises a signal output section for outputting a signal representing a characteristic of a measurement specimen prepared by mixing a sample with a reagent, and a signal adjusting section for adjusting the signal outputted from the signal output section, the measuring unit configured to output a detection signal based on the signal adjusted by the signal adjusting section; and a result producing unit for producing an analysis result based on the detection signal outputted from the measuring unit and storing the analysis result, wherein the computer program product comprising a computer readable medium storing instructions adapted to enable the result producing unit to carry out operations, comprising: a step of extracting an analysis result of a sample meeting a predetermined requirement from a plurality of stored analysis results; a step of calculating an adjustment value used in the signal adjustment by the signal adjusting section based on the extracted analysis result; and a step of transmitting the calculated adjustment value to the measuring unit.

A third aspect of the presented invention is a method for analyzing a sample, comprising: extracting analysis results of samples, each of the samples meeting a predetermined requirement, from a memory; calculating an adjustment value based on the extracted analysis results; obtaining a signal representing a characteristic of a measurement specimen prepared by mixing a sample with a reagent; adjusting the signal based on the calculated adjustment value; and producing an analysis result of the sample based on the signal adjusted by the adjustment value.

BRIEF DESCRIPTION OF THE DRAWINGS

FIG. 4 is an example diagram illustrating a data configuration stored in an analysis result storing unit of the sample analyzer according to the embodiment of the present invention;

FIG. 6 is a flow chart illustrating adjustment value calculating steps carried out by a CPU of the controller provided in the computing display apparatus of the sample analyzer according to the embodiment of the present invention;

FIGS. 7A and 7B are diagrams for describing a gain adjustment value calculation method, which illustrate scattergrams respectively showing analysis results obtained by analyzing white blood cells in DIFF mode;

FIG. 11 is an example diagram illustrating a data configuration stored in an analysis result storing unit according to another embodiment of the present invention;

DETAILED DESCRIPTION OF THE PREFERRED EMBODIMENTS

Hereinafter, an embodiment of a sample analyzer of the present invention will be described in detail with reference to the accompanying drawings.

Referring to the accompanying drawings, the present embodiment will be described in detail below using a blood analyzer as an example, wherein cell components included in blood collected as a sample are sorted into different groups such as red blood cells (RBC), white blood cells (WBC), and platelets (PLT) and then accordingly counted. It is needless to say that the sample is not limited to blood.

Figure 1:
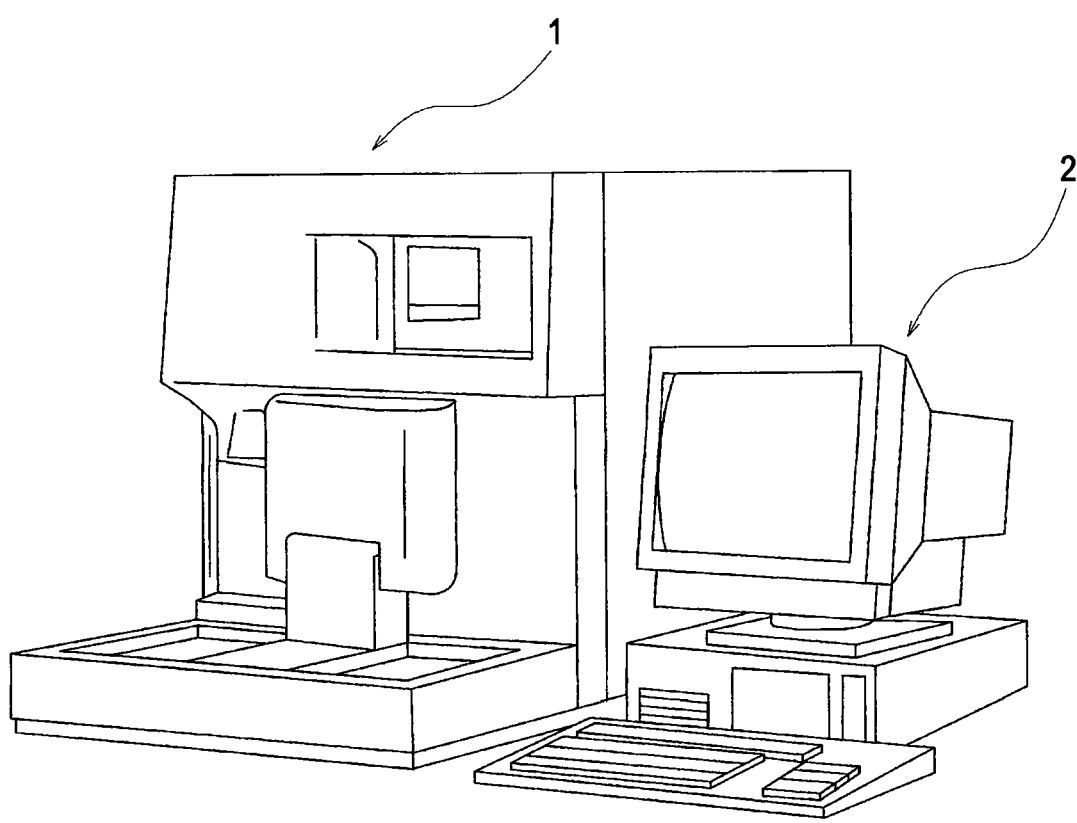
FIG. 1 is a perspective view schematically illustrating a structure of a sample analyzer according to an embodiment of the present invention.

FIG. 1 is a perspective view schematically illustrating a structure of a sample analyzer according to the embodiment of the present invention. As illustrated in FIG. 1, the sample analyzer according to the present embodiment has a measuring apparatus (measuring unit) 1, and a computing display apparatus (result producing unit) 2 connected to the measuring apparatus 1 to enable data communication therebetween.

The measuring apparatus 1 and the computing display apparatus 2 are connected to each other by a communication line (not illustrated). When these apparatuses communicate data therebetween, the computing display apparatus 2 controls an operation of the measuring apparatus 1, and the computing display apparatus 2 processes measurement data obtained by the measuring apparatus 1 to obtain an analysis result. The measuring apparatus 1 and the computing display apparatus 2 may be connected to each other by a network.

These apparatuses may constitute a single apparatus as an integral unit to communicate data therebetween through an inter-process communication system or the like.

The measuring apparatus 1 uses a flow cytometry method to detect characteristic information of, for example, white blood cells and reticulocytes in blood, and transmits the detected result to the computing display apparatus 2 as a detection signal. The flow cytometry method is a method wherein a specimen flow including a measurement specimen is developed and the specimen flow is irradiated with laser light to detect light such as forward scattered light, side scattered light, or side fluorescence emitted by particles (hemocytes) in the measurement specimen, so that the particles (hemocytes) in the measurement specimen are detected.

Figure 2:
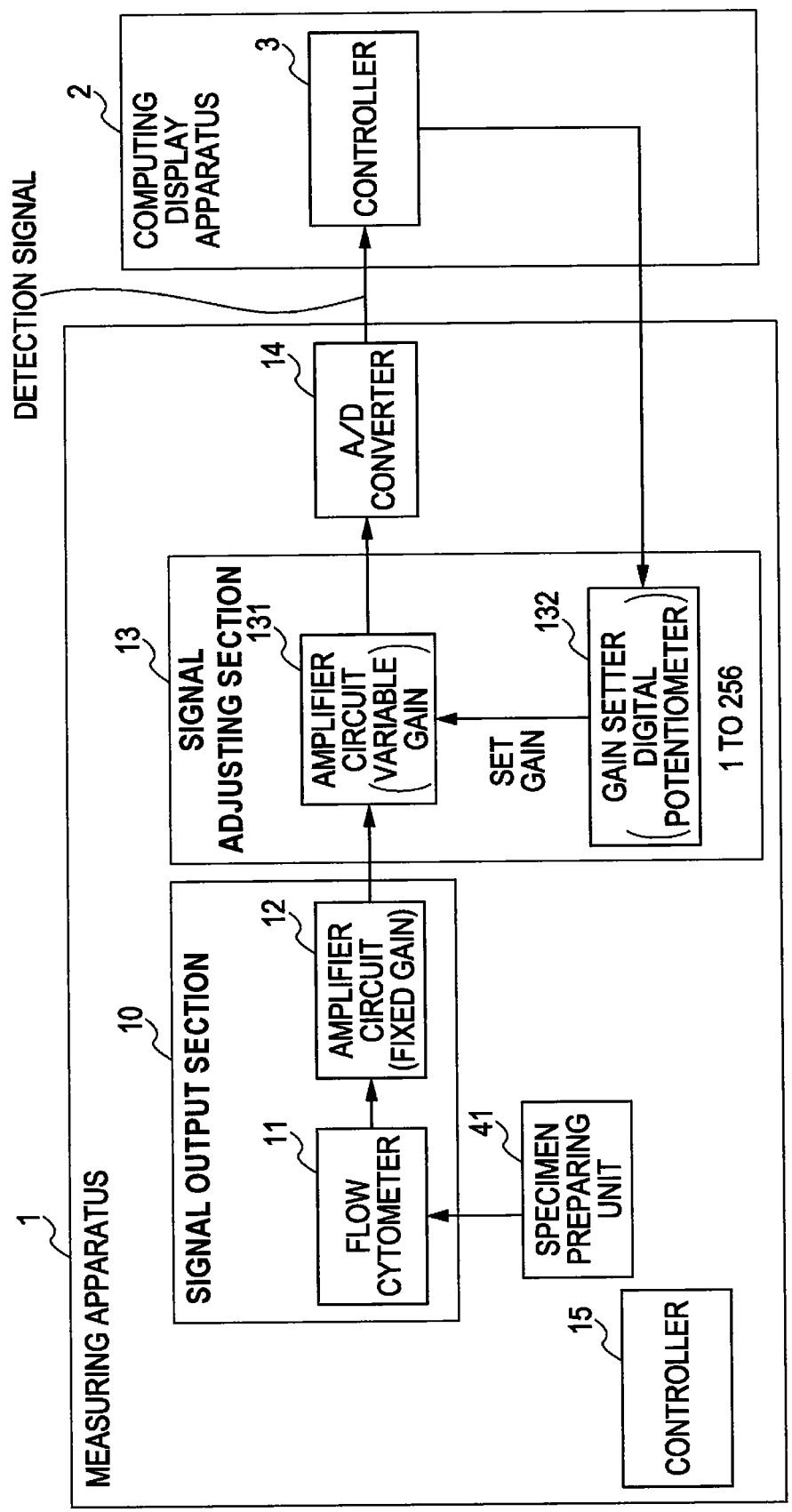
FIG. 2 is a block diagram illustrating the structure of the sample analyzer according to the embodiment of the present invention.

FIG. 2 is a block diagram illustrating the structure of the sample analyzer according to the embodiment of the present invention. The measuring apparatus 1 has a flow cytometer 11 which detects characteristic information of, for example, white blood cells and reticulocytes in blood, using the flow cytometry method and outputs an electrical signal obtained by photo-electrically converting the characteristic information, an amplifier circuit 12 which amplifies the electrical signal outputted from the flow cytometer 11, a signal adjusting section 13 which adjusts a gain in order to adjust a detection sensitivity to finally adjust the magnitude of an output signal, an A/D converter 14 which A/D-converts the adjusted output signal into a digital signal and outputs the digital signal as a detection signal, and a controller 15 including a CPU or the like which controls the operations of these hardware units. The flow cytometer 11 and the amplifier circuit 12 constitute a signal output section 10. The measuring apparatus 1 further has a specimen preparing unit 41 which prepares a measurement specimen and supplies the prepared measurement specimen to the flow cytometer 11.

Figure 14:
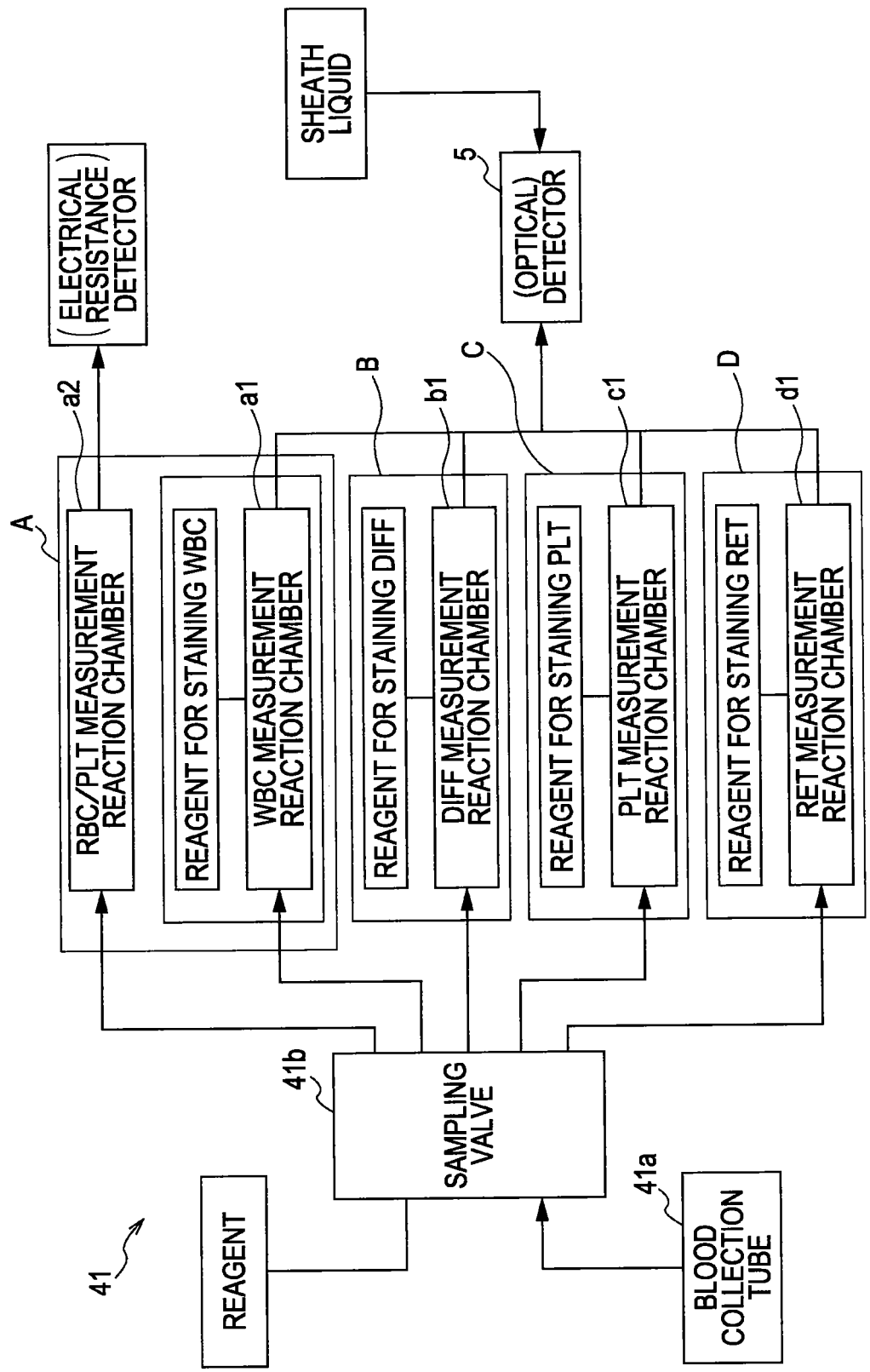
FIG. 14 is a block diagram illustrating a structure of a specimen preparing unit provided in the sample analyzer according to the present embodiment.

FIG. 14 is a block diagram schematically illustrating a structure of the specimen preparing unit 41. The specimen preparing unit 41 has a sampling valve 41b which determines the quantity of blood suctioned from a blood collection tube 41a, and a plurality of reaction blocks A to D used to prepare different measurement specimens in preset measurement modes.

The specimen preparing unit 41 has a CBC measurement reaction block A which prepares specimens for measuring CBC, a DIFF measurement reaction block B which prepares a specimen for measuring DIFF, a PLT measurement reaction block C which prepares a specimen for measuring PLT, and a RET measurement reaction block D which prepares a specimen for measuring RET.

The CBC measurement reaction block A prepares specimens for measuring WBC, RBC and PLT. More specifically, the CBC measurement reaction block A serves as a mechanism for preparing the specimen for measuring white blood cells (WBC), equipped with a reagent for staining WBC, and a WBC measurement reaction chamber a1. The CBC measurement reaction block A also serves as a mechanism for preparing the specimens for measuring red blood cells (RBC) and platelets (PLT), equipped with an RBC/PLT measurement reaction chamber a2.

The DIFF measurement reaction block B serves as a mechanism for preparing the specimen for measuring DIFF, equipped with a reagent for staining DIFF, and a DIFF measurement reaction chamber b1.

The PLT measurement reaction block C serves as a mechanism for preparing the specimen for measuring PLT, equipped with a reagent for staining PLT, and a PLT measurement reaction chamber c1.

The RET measurement reaction block D serves as a mechanism for preparing the specimen for measuring RET, equipped with a reagent for staining RET, and a RET measurement reaction chamber d1.

The RBC/PLT measurement reaction chamber a2 is connected to the sampling valve 41b so that the reagent is mixed with the blood quantitatively defined by the sampling valve 41b. The RBC/PLT measurement reaction chamber a2 is connected to an electrical resistance detecting unit so that the measurement specimen prepared in the RBC/PLT measurement reaction chamber a2 is supplied to the electrical resistance detecting unit.

The reaction chambers a1 to d1 are each connected to the sampling valve 41b to mix a prescribed volume of staining solution with the mixture obtained by mixing the reagent with the blood whose quantity was determined by the sampling valve 41b. The reaction chambers a1 to d1 are each connected to the flow cytometer 11 to supply the measurement specimen prepared by mixing the prescribed reagent and the staining solution with the blood to the flow cytometer 11.

When the specimen is thus prepared in the WBC measurement reaction chamber a1 of the CBC measurement reaction block A, the specimen preparing unit 41 can prepare a measurement specimen in which white blood cells are stained and red blood cells are hemolyzed as a WBC measuring specimen.

When the specimen is thus prepared in the DIFF measurement reaction chamber b1 of the DIFF measurement reaction block B, the specimen preparing unit 41 can prepare a measurement specimen in which WBC subclasses are stained to generate fluorescent differences in accordance with their different types and red blood cells are hemolyzed as a DIFF measuring specimen.

When the specimen is thus prepared in the RET measurement reaction chamber d1 of the RET measurement reaction block D, the specimen preparing unit 41 can prepare a measurement specimen in which reticulocytes are stained as a RET measuring specimen.

When the specimen is thus prepared in the PLT measurement reaction chamber c1 of the PLT measurement reaction block C, the specimen preparing unit 41 can prepare a measurement specimen in which platelets are stained as a PLT measuring specimen.

The respective measurement specimens thus prepared are supplied to a flow cell 503 of the flow cytometer 11, which will be described later, along with a sheath liquid.

Figure 3:
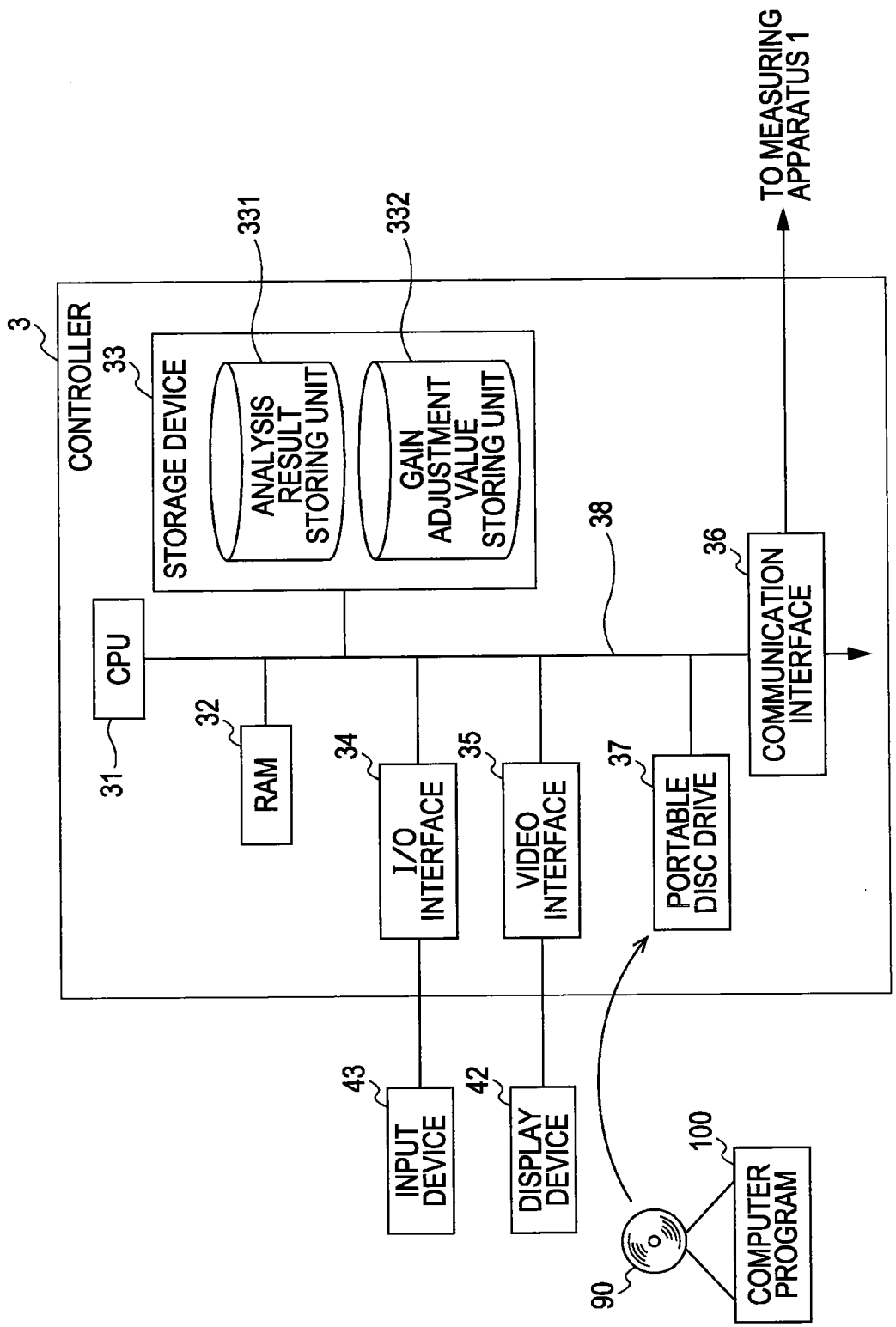
FIG. 3 is a block diagram illustrating a structure of a controller provided in a computing display apparatus of the sample analyzer according to the embodiment of the present invention.

A controller 3 of the computing display apparatus 2 calculates a suitable adjustment value based on a signal outputted from the measuring apparatus 1 and notifies the measuring apparatus 1 of the calculated adjustment value. FIG. 3 is a block diagram illustrating a structure of the controller 3 provided in the computing display apparatus 2 of the sample analyzer according to the embodiment of the present invention.

An arithmetic central processing unit, such as CPU, constitutes the controller 3 of the computing display apparatus 2. The controller 3 has at least a CPU (central processing unit) 31, a memory 32, a storage device 33, an I/O interface 34, a video interface 35, a communication interface 36, a portable disc drive 37, and an internal bus 38 provided to connect the hardware units described above. The CPU 31 is connected to the hardware units of the controller 3 by way of the internal bus 38 to control the operations of the hardware units, and also controls the operation of the measuring apparatus 1 in accordance with a computer program 100 stored in the storage device 33.

An example of the memory 32 is a non-volatile memory such as SRAM or flash memory. A load module is developed when the computer program 100 is executed so that the memory 32 stores therein temporary data and the like produced when the computer program 100 is executed.

An example of the storage device 33 is a built-in stationary storage device (hard disc). The computer program 100 stored in the storage device 33 is downloaded into the portable disc drive 37 from a portable recording medium 90 such as DVD or CD-ROM where information such as programs and data are recorded. When the computer program is executed, it is read from the storage device 33 into the memory 32 and executed. The computer program may be a computer program downloaded from an external computer through the communication interface 36.

The communication interface 36 is connected to the internal bus 38. The communication interface 36, when connected to an external network such as the Internet, LAN, or WAN, can transmit and receive data to and from an external computer, the measuring apparatus 1, and the like. For example, the storage device 33 is not necessarily mounted in the controller 3. The storage device 3 may be an external recording medium, for example, an external storage connected to the controller 3 through the communication interface 36.

The I/O interface 34 is connected to an input device 43 including, for example, a keyboard and a mouse. The video interface 35 is connected to a display device 42 such as CRT monitor or LCD.

The storage device 33 has an analysis result storing unit 331, and a gain adjustment value storing unit 332. In the analysis result storing unit 331, analysis results of different samples are stored after they are linked to their sample IDs used to identify the respective samples. FIG. 4 is an example diagram illustrating a data configuration stored in the analysis result storing unit 331 of the sample analyzer according to the embodiment of the present invention.

As illustrated in FIG. 4, the analysis result storing unit 331 stores therein various analysis results and sample measurement dates which are linked to the sample IDs used to identify the samples. In the example illustrated in FIG. 4, the analysis results stored in the analysis result storing unit 331 are LYMPH-X and NEUT-Y.

Here, "LYMPH-X" denotes a value on X-axis at the center of mass in a cluster of lymphoid corpuscles, which is an analysis result obtained by measuring the white blood cell in the DIFF measurement mode (intensity of side scattered light). "NEUT-Y" denotes a value on Y-axis at the center of mass in a cluster of neutrophil leucocytes, which is an analysis result obtained by measuring the white blood cell in the DIFF measurement mode (intensity of side fluorescence).

In the gain adjustment value storing unit 332, gain adjustment values calculated based on analysis results of a sample meeting a predetermined requirement are stored after they are linked to the respective measurement items. Therefore, the gain adjustment values may be frequently updated for some of the measurement items, whereas they may be scarcely updated for the other measurement items. The controller 3 of the computing display apparatus 2 transmits the adjustment values stored in the gain adjustment value storing unit 332 to the measuring apparatus 1. Based on the adjustment value transmitted from the computing display apparatus 2, the measuring apparatus 1 adjusts the signal outputted from the signal output section 10 using the signal adjusting section 13.

Figure 5:
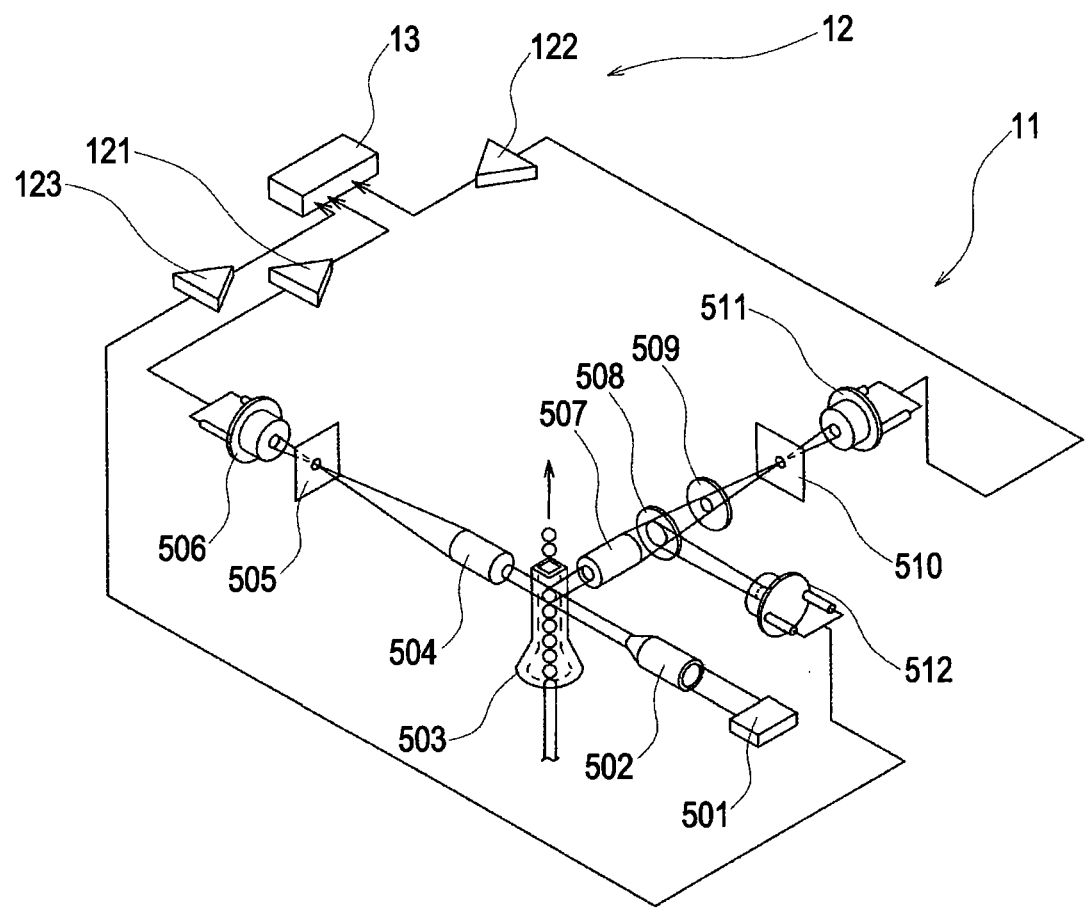
FIG. 5 is a block diagram schematically illustrating structures of a flow cytometer, a light receiving element, and an amplifier circuit provided in the sample analyzer according to the embodiment of the present invention.

FIG. 5 is a block diagram schematically illustrating structures of the flow cytometer 11 and the amplifier circuit 12 provided in the sample analyzer according to the embodiment of the present invention. As illustrated in FIG. 5, the flow cytometer 11 has a light emitter (light source) 501 which is a light source for emitting laser light; an irradiation lens unit 502; a sheath flow cell 503 which is irradiated with the laser light; a condensing lens 504, a pin hole 505, and a PD (photodiode) 506 (a beam stopper, which is not illustrated, is disposed between the sheath flow cell 503 and the condensing lens 504), which are arranged on a straight line extending in a direction in which the laser light emitted from the light emitter 501 advances; and a condensing lens 507, a dichroic mirror 508, an optical filter 509, a pin hole 510, an APD (avalanche photodiode) 511, and a PD (photodiode) 512 disposed on the lateral side of the dichroic mirror 508, which are arranged in a direction intersecting with the direction in which the laser light emitted from the light emitter 501 advances.

The light emitter 501 is provided to emit the laser light to the specimen flow including the measurement specimen passing through the sheath flow cell 503. The irradiation lens unit 502 is provided to irradiate the specimen flow with the laser light emitted from the light emitter 501. The PD 506 is provided to receive the forward scattered light emitted from the sheath flow cell 503. The forward scattered light emitted from the sheath flow cell 503 provides information of the sizes of particles (hemocytes) in the measurement specimen.

The dichroic mirror 508 is provided to separate the side scattered light and the side fluorescence emitted from the sheath flow cell 503 from each other. More specifically, the dichroic mirror 508 is provided so that the side scattered light emitted from the sheath flow cell 503 enters the PD 512 and the side fluorescence emitted from the sheath flow cell 503 enters the APD 511. The PD 512 is provided to receive the side scattered light. The side scattered light emitted from the sheath flow cell 503 supplies information of the sizes of particles (hemocytes) in the measurement specimen.

The APD 511 is provided to receive the side fluorescence. When a fluorescent material such as stained hemocytes is irradiated with light, light having a wavelength longer than that of the irradiated light is emitted therefrom. The intensity of side fluorescence is increased as the component is more deeply stained. Therefore, characteristic information relating to the staining density of hemocytes is obtained by measuring the intensity of side fluorescence emitted from the sheath flow cell 503. The PDs 506 and 512 and APD 511 convert respective optical signals that they received into electrical signals and amplify the electrical signals in amplifier circuits 121, 123 and 122, and then output the amplified signals to the signal adjusting section 13.

Returning to FIG. 2, the signal adjusting section 13 includes a gain setter 132 which obtains the adjustment value calculated by the computing display apparatus 2 and sets a gain based on the obtained adjustment value, and an amplifier circuit 131 which corrects the electrical signal outputted from the amplifier circuit 12 based on the set gain. The gain setter 132 is a digital potentiometer, which sets the gain suitable for the obtained adjustment value to any value included in the numeral range of 1 to 256. The amplifier circuit 131 amplifies the electrical signal outputted from the amplifier circuit 12 based on the set gain, and outputs the amplified electrical signal as an output signal to the A/D converter 14.

In the present embodiment, the computing display apparatus 2 calculates the suitable adjustment value based on the analysis result and transmits the calculated adjustment value to the measuring apparatus 1. Accordingly, sensitivity is automatically adjusted. To suitably calculate the adjustment value, it is necessary to collect the analysis results of any samples having a homogenous characteristic from all of the past analysis results to calculate an analysis result that can be used as a judgment criterion. However, samples generally include many different factors such as sex and age, which makes it difficult to find homogeneity in most of the samples. Accordingly, it is difficult to calculate a suitable adjustment value. According to the present embodiment, therefore, to relieve a user of the time-consuming burden of searching homogenous samples, the computing display apparatus 2 extracts the analysis results of a sample meeting a predetermined requirement to calculate the adjustment value.

FIG. 6 is a flow chart illustrating adjustment value calculating processing steps carried out by a CPU 31 of the controller 3 provided in the computing display apparatus 2 of the sample analyzer according to the embodiment of the present invention. In FIG. 6, when the CPU 31 of the controller 3 of the computing display apparatus 2 detects that the computing display apparatus 2 was turned on, the CPU 31 executes an initializing process (initializes a program) (step S601), and displays a menu screen on the display apparatus 42 (S602). The menu screen can accept various inputs, for example, input of measurement order, selection of measurement mode such as CBC mode, CBC+DIFF mode, or RET mode, command to start measurement, shutdown command, and command to adjust sensitivity.

The CPU 31 determines whether or not the command to adjust sensitivity was inputted (S603). The sensitivity adjustment command may be inputted via the menu screen displayed on the display device 42 by manipulating the input device 43 such as mouse, however, may be inputted in any arbitrary way. When determined that the sensitivity adjustment command was inputted (step S603: YES), the CPU 31 extracts the analysis result of a sample meeting a predetermined requirement from the analysis result storing unit 331 (step S604).

For example, whether or not a sample meets a predetermined requirement is determined by whether or not an analysis result obtained therefrom stays within a predetermined numeral range set for its target value. Taking for instance the analysis result obtained through measurement in the DIFF mode, LYMPH-X representing the intensity of side scattered light at the center of mass in a cluster of lymphoid corpuscles (LYMPH), and NEUT-Y representing the intensity of side fluorescence at the center of mass in a cluster of neutrophil leucocytes (NEUT) are calculated. Then, it is determined whether or not LYMPH-X and NEUT-Y stay in predetermined numeral ranges respectively set for their target values.

More specifically, it is determined whether or not LYMPH-X stays in the range of 88.0±3.2, and whether or not NEUT-Y stays in the range of 43.5±2.0. Any samples having the analysis results close to the respective target values are determined as homogenous, and the adjustment value is accordingly calculated. As a result, the gain can be suitably adjusted for the output signal of the measuring apparatus 1.

The CPU 31 calculates the gain adjustment value based on the extracted analysis result (step S605). FIGS. 7A and 7B are diagrams for describing a gain adjustment value calculation method, which respectively illustrate scattergrams showing analysis results obtained by analyzing the white blood cell in the DIFF mode. FIG. 7A schematically illustrates a scattergram showing a region where a plot of white blood cells are distributed. FIG. 7B schematically illustrates a scattergram in the case where the region where a plot of white blood cells are distributed is off a target position. In FIGS. 7A and 7B, a vertical axis (Y-axis) represents the intensity of side fluorescence, and a horizontal axis (X-axis) represents the intensity of side scattered light.

As illustrated in FIGS. 7A and 7B, in the scattergram created when the white blood cells are counted in the DIFF mode, the distribution of a plot of white blood cells is concentrated on five clusters, which are a cluster of monocytes (MONO) 71, a cluster of lymphocytes (LYMPH) 72, a cluster of basocytes (BASO) 73, a cluster of neutrophils (NEUT) 74, and a cluster of eosinocyte (EO) 75. Assuming that the state illustrated in FIG. 7A is a target state, in the state illustrated in FIG. 7B, the cluster of lymphocytes (LYMPH) 72 is too close to the cluster of monocytes (MONO) 71, and the cluster of neutrophils (NEUT) 74 is too close to the cluster of eosinocyte (EO) 75, making it difficult to confirm inter-cluster boundaries. As a result, the respective plots that are not distinctly distinguished from one another may not be accurately sorted and counted.

In view of the above, the gain is adjusted so that the intensity of side scattered light represented by X-axis is amplified and the intensity of side fluorescence represented by Y-axis is amplified. Accordingly, the cluster of lymphocytes (LYMPH) 72 can be separated from the cluster of monocytes (MONO) 71, and the cluster of neutrophils (NEUT) 74 can be separated from the cluster of eosinocyte (EO) 75. More specifically, as to the intensity of side scattered light, a displacement 76 is calculated from the center-of-mass position and the targeted value of the intensity of side scattered light of the cluster of lymphocytes (LYMPH) 72. The displacement 76 is the gain adjustment value of the intensity of side scattered light (hereinafter, referred to as adjustment value X). As to the intensity of side fluorescence, a displacement 77 is calculated from the center-of-mass position and the targeted value of the intensity of side fluorescence of the cluster of neutrophils (NEUT) 74. The displacement 77 is the gain adjustment value of the intensity of side fluorescence (hereinafter, referred to as adjustment value Y). Thus, the gain adjustment value of the intensity of side scattered light (adjustment value X) and the gain adjustment value of the intensity of side fluorescence (adjustment value Y) are separately calculated. The adjustment value can be calculated as far as at least one analysis result can be obtained from the sample meeting a predetermined requirement.

Returning to FIG. 6, the CPU 31 of the controller 3 of the computing display apparatus 2 updates the adjustment value stored in the gain adjustment value storing unit 332 to the calculated adjustment value (step S606). The CPU 31, when transmitting a measurement command signal to the measuring apparatus 1, transmits the calculated adjustment value as well as the command signal. When determined that the sensitivity adjustment command was not received (step S603: NO), the CPU 31 proceeds to step S811 illustrated in FIG. 8 described later.

Figure 8:
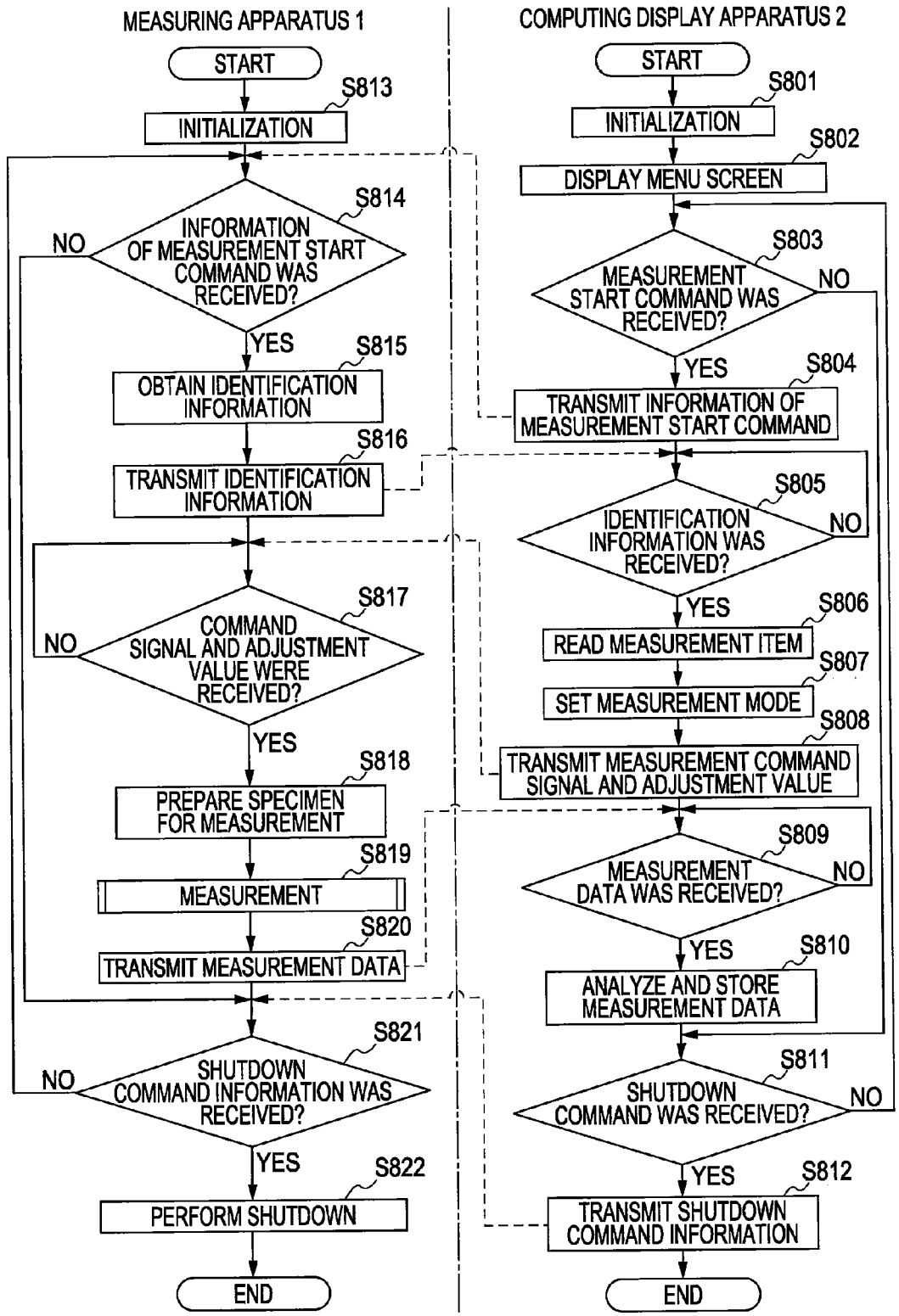
FIG. 8 is a flow chart illustrating processing steps carried out by a controller of a measuring apparatus and the CPU of the controller of the computing display apparatus provided in the sample analyzer according to the embodiment of the present invention.

FIG. 8 is a flow chart illustrating processing steps carried out by the controller 15 of the measuring apparatus 1 and the CPU 31 of the controller 3 of the computing display apparatus 2 provided in the sample analyzer according to the embodiment of the present invention.

When the controller 15 of the measuring apparatus 1 detects that the measuring apparatus 1 was turned on, the controller 51 performs an initializing process (step S813), and checks the operations of the respective devices of the measuring apparatus 1. The CPU 31 of the controller 3 of the computing display apparatus 2 also performs an initializing process (initializes a program) (step S801) when detecting that the computing display apparatus 2 was turned on, and displays a menu screen on the display device 42 (step S802). The menu screen can accept various inputs, for example, input of measurement order, selection of measurement mode such as CBC mode, CBC+DIFF mode, and RET mode, command to start measurement, shutdown command, and command to adjust sensitivity.

The CPU 31 of the controller 3 of the computing display apparatus 2 determines whether or not the measurement start command was received (step S803). When determined that the measurement start command was not received (step S803: NO), the CPU 31 skips the processing steps of step S804 to step S810. When determined that the measurement start command was received (step S803: YES), the CPU 31 transmits command information which commands to start the measurement to the measuring apparatus 1 (step S804). The controller 15 of the measuring apparatus 1 determines whether or not the command information which commands to start the measurement was received (step S814). When determined that the command information which commands to start the measurement was received (step S814: YES), the controller 15 reads a barcode label (not illustrated) attached to a container in which blood is housed using a barcode reader (not illustrated) to obtain identification information of the blood (specimen ID) (step S815). When determined that the command information which commands to start the measurement was not received (step S814: NO), the controller 15 skips the processing steps of step S815 to step S820.

The controller 15 transmits the obtained identification information (specimen ID) to the computing display apparatus 2 (step S816), and the CPU 31 of the controller 3 of the computing display apparatus 2 determines whether or not the identification information (specimen ID) was received (step S805). When determined that the identification information (specimen ID) was not received (step S805: NO), the CPU 31 becomes a reception standby state. When determined that the identification information (specimen ID) was received (step S805, YES), the CPU 31 checks the storage device 33 based on the received identification information (specimen ID) to read the measurement item included in the measurement order stored therein which is linked to the identification information (specimen ID) (step S806), sets the measurement mode based on the read the measurement item (step S807), and transmits signals which command to prepare and measure the measurement specimen in accordance with the set measurement mode, and the gain adjustment value stored in the gain adjustment value storing unit 332 to the measuring apparatus 1 (step S808).

The above processing steps are described in detail below. The storage device 33 of the controller 3 of the computing display apparatus 2 stores therein reagents used to prepare the measurement specimens in accordance with the different measurement modes in the form of, for example, a table. When the measurement mode is set in step S807, the CPU 31 checks the storage device 33 using the set measurement mode as key information, and decides which of the reagents (reaction blocks) is used to prepare the measurement specimen. The CPU 31 prepares the measurement specimen using the decided reaction block, and transmits a signal which commands to measure the prepared measurement specimen to the controller 15 of the measuring apparatus 1 together with the gain adjustment value stored in the gain adjustment value storing unit 332. More specifically, when the DIFF mode is set, the CPU 31 transmits a signal which command to prepare the measurement specimen in the DIFF measurement reaction block b1, and a signal which commands to measure the prepared measurement specimen using the flow cytometer 11 to the controller 15. At the time, the CPU 31 reads the gain adjustment value used for the measurement in the DIFF mode from the gain adjustment value storing unit 332, and transmits the read signal together with the command signals to the controller 15. The gain adjustment value transmitted to the controller 15 includes the gain adjustment value (adjustment value X) for a side scattered light signal and the gain adjustment value (adjustment value Y) for a side fluorescence signal.

The description given above refers to the example in which the DIFF mode is set as the measurement mode. When the RET mode is set as the measurement mode, for example, the gain adjustment value, which is determined in advance as a value specific to the RET mode, is read from the gain adjustment value storing unit 332 and transmitted to the controller 15 of the measuring apparatus 1.

The measurement mode thus set is stored in the storage device 33 of the controller 3 of the computing display apparatus 2.

Next, the controller 15 of the measuring apparatus 1 determines whether or not the command signals and the adjustment value were received (step S817). When determined that these signal were not received (step S817: NO), the controller 15 becomes a reception standby state. When determined that these signal were received (step S817: YES), the controller 15 controls the specimen preparing unit so that the measurement specimen corresponding to the received measurement mode is prepared (step S818), and starts to measure the prepared measurement specimen.

As described above, a signal outputted as a measurement result of the measurement specimen is outputted as an electrical signal corresponding to the intensity of the side scattered light, side fluorescence, or forward scattered light. The outputted electrical signal is amplified in the amplifier circuit 12 based on a fixed gain and also amplified in the signal adjusting section 13 based on a set gain. Then, the electrical signal is converted into, for example, a 12-bit digital signal in the A/D converter 14 and outputted to the controller 15 as a detection signal. The gain adjustment value transmitted from the computing display apparatus 2 in step S808 illustrated in FIG. 9 includes the gain adjustment value (adjustment value X) for the side scattered light signal and the gain adjustment value (adjustment value Y) for the side fluorescence signal. The signal adjusting section 13 amplifies the side scattered light signal based on the adjustment value X, and amplifies the side fluorescence signal based on the adjustment value Y. The controller 15 transmits the received detection signal to the computing display apparatus 2 as measurement data (step S820).

Figure 9:
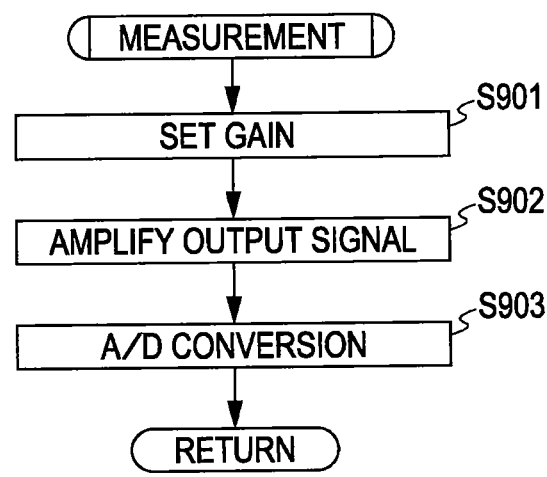
FIG. 9 is a flow chart illustrating measuring steps carried out in step S819 of FIG. 8 by the controller of the measuring apparatus provided in the sample analyzer according to the embodiment of the present invention.

FIG. 9 is a flow chart illustrating the measurement step carried out in step S819 of FIG. 8 by the controller 15 of the measuring apparatus 1 of the sample analyzer according to the embodiment of the present invention. In FIG. 9, the controller 15 of the measuring apparatus 1 sets the gain in the form of a digital value based on the received adjustment value (step S901), and amplifies the output signal (step S902).

The controller 16 A/D-converts the amplified output signal (step S903), and returns the process to step S820 illustrated in FIG. 8.

Returning to FIG. 8, the CPU 31 of the controller 3 of the computing display apparatus 2 determines whether or not the measurement data was received (step S809). When determined that the measurement data was not received (step S809: NO), the CPU 31 becomes the reception standby state. When determined that the measurement data was received (step S809: YES), the CPU 31 analyzes the received measurement data and stores the analysis result in the analysis result storing unit 331 (step S810).

The CPU 31 determines whether or not a shutdown command was received (step S811). When determined that the shutdown command was not received (step S811: NO), the CPU 31 returns the process to step S803 to repeat the above processing step. When determined that the shutdown command was received (step S811: YES), the CPU 31 transmits information of the shutdown command to the measuring apparatus 1 (step S812).

The controller 15 of the measuring apparatus 1 determines whether or not the shutdown command information was received (step S821). When determined that the shutdown command information was not received (step S821: NO), the controller 15 returns the process to step S814 to repeat the above processing step. When determined that the shutdown command information was received (step S821: YES), the controller 15 shuts down the system (step S822) to end the processing steps.

Figure 10:
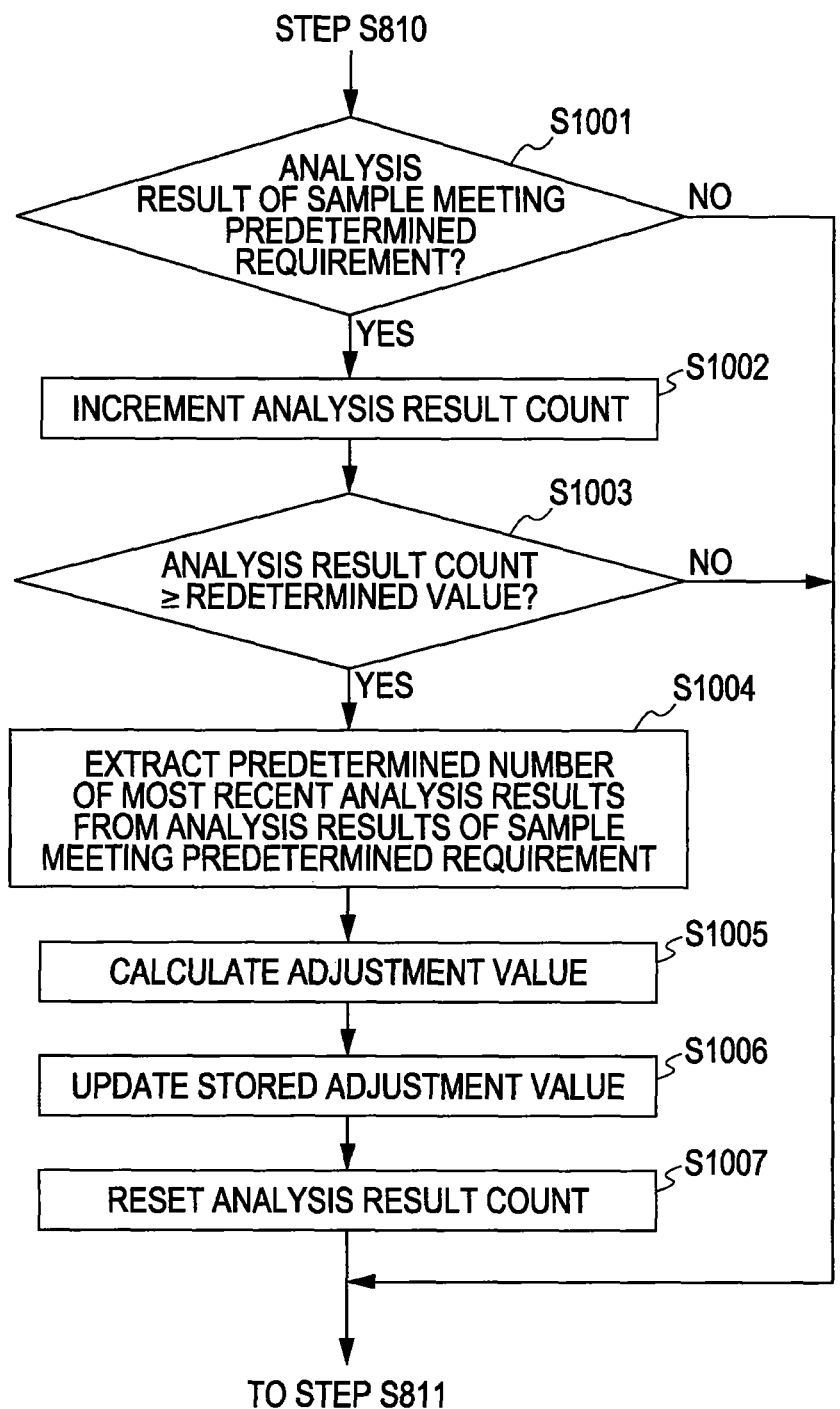
FIG. 10 is a flow chart illustrating automatic signal adjusting steps carried out by the CPU of the controller of the computing display apparatus provided in the sample analyzer according to the embodiment of the present invention.

In the processing step described above, the adjustment value is calculated in the case where the command to adjust sensitivity was received so that the signal is adjusted. For example, the above processing step may be automatically carried out to adjust the signal in the case where the analysis result of a sample meeting a predetermined requirement is obtained. FIG. 10 is a flow chart illustrating automatic signal adjusting steps carried out by the CPU 31 of the controller 3 of the computing display apparatus 2 provided in the sample analyzer according to the embodiment of the present invention.

After the analysis result was stored in the analysis result storing unit 331 in step S810 of FIG. 8, the CPU 31 of the controller 3 of the computing display apparatus 2 determines whether or not the stored analysis result is the analysis result of a sample meeting a predetermined requirement (step S1001). When determined that the stored analysis result is not the analysis result of the sample meeting a predetermined requirement (step S1001: NO), the CPU 31 skips the processing steps in step S1002 to step S1007, and proceeds to step S811 illustrated in FIG. 8.

When determined that the stored analysis result is the analysis result of the sample meeting a predetermined requirement (step S1001: YES), the CPU 31 increments a count value of the analysis result of the sample meeting a predetermined requirement (hereinafter, referred to as analysis result count) by "1" (step S1002). The CPU 31 determines whether or not the analysis result count is at least a predetermined value, for example, "10" (step S1003). When determined that the analysis result count is smaller than the predetermined value (step S1003: NO), the CPU 31 skips the processing steps in step S1004 to step S1007, and proceeds to step S811 of FIG. 8.

When determined that the analysis result count is equal to or larger than the predetermined value (step S1003: YES), the CPU 31 extracts from the analysis result storing unit 331 a predetermined number of analysis results most recently stored, for example, ten analysis results, from all of the stored analysis results of the sample meeting a predetermined requirement (S1004). In a manner similar to the processing step of step S605 illustrated in FIG. 6, the CPU 31 calculates the gain adjustment value based on the predetermined number of sample analysis results thus extracted (step S1005). More specifically, as described with reference to FIG. 7, displacements for adjusting the intensity of side scattered light and the intensity of side fluorescence to their target values are obtained for all of the predetermined number of analysis results. Then, a mean value of the displacements obtained from the predetermined number of sample analysis results is calculated to obtain the adjustment value.

In a manner similar to step S606 illustrated in FIG. 6, the CPU 31 updates the stored adjustment value to a newly calculated adjustment value (step S1006). The CPU 31 resets the analysis result count (step S1007), and then proceeds to step S811 illustrated in FIG. 8.

The automatic calculation of the adjustment value described above can make it unnecessary for the user to command to update the adjustment value.

In the description, "10" is given as an example of the predetermined number, however, any arbitrary number of analysis results can be extracted. By setting the predetermined number to "1", for example, when the analysis result of the sample meeting a predetermined requirement is generated and stored, the stored analysis result of the sample meeting a predetermined requirement can be extracted automatically to calculate the adjustment value. Accordingly, the adjustment value can constantly retain a suitable value.

In a case where the predetermined number is set to "1", the processing steps of step S1002, step S1003, and step S1007 in FIG. 10 can be omitted.

In the description given above, the analysis results of the sample meeting a predetermined requirement are counted, however, the present invention is not necessarily limited thereto. For example, every time when the analysis result of the sample meeting a predetermined requirement is stored in the analysis result storing unit 331, the analysis result of the sample meeting a predetermined requirement is extracted from the analysis result storing unit 331 to be stored in another database, and the adjustment value may be calculated based on the analysis results stored in the database when a predetermined number of analysis results are stored therein.

As described above, according to the present embodiment, a sample analyzer using a light receiving element can adjust a signal representing a characteristic of a measurement specimen using a gain adjustment value calculated based on the analysis result of a sample meeting a predetermined requirement. Therefore, it is unnecessary for the user to perform such a time-consuming work of searching the analysis results of the sample having a particular characteristic in a huge volume of analysis results. The signal is simply adjusted to flexibly respond to the circumstances of a site where the sample analyzer is used. As a result, an analysis result can be obtained based on the signal thus appropriately adjusted.

In the above-described embodiment, there is described an example of extracting the sample analysis result whose LYMPH-X and NEUT-Y mean values respectively stay in the predetermined numeral ranges for their target values as the analysis result of the sample meeting a predetermined requirement. However, the present invention is not necessarily limited thereto. For example, the analysis result of the sample meeting a predetermined requirement that can be extracted may be an analysis result of a CBC-measured sample, in which hemoglobin concentration (HGB), mean corpuscular volume (MCV), count of white blood cells (WBC), and count of platelets (PLT) obtained from the CBC analysis respectively stay within their predetermined numeral ranges. This embodiment is described with reference to FIG. 11.

FIG. 11 is an example diagram illustrating a data configuration stored in an analysis result storing unit according to a modified embodiment of the present invention. As illustrated in FIG. 11, the analysis result storing unit 331 stores therein CBC analysis results (HGB, MCV, WBC, and PLT) and DIFF analysis results (LYMPH-X and NEUT-Y) which are linked to sample IDs used to identify samples.

In step S604 illustrated in FIG. 6, the CPU 31 extracts analysis results that meet the following requirements (1) to (4) from the analysis result storing unit 331 as the analysis result of the sample meeting a predetermined requirement.

(1) HGB is included in a predetermined numeral range.
(2) MCV is included in a predetermined numeral range.
(3) WBC is included in a predetermined numeral range.
(4) PLT is included in a predetermined numeral range.

The CPU 31 calculates the adjustment value in step S605 using the DIFF analysis results (LYMPH-X and NEUT-Y) included in the extracted analysis results. The adjustment value is calculated in the same manner as described in the above embodiment.

The following requirement may be added to the requirements for extracting the analysis result; a sample still very fresh should be extracted, that is, the sample to be extracted is a sample measured within a predetermined period of time after it is collected. Specifically, this can be realized as follows.

Figure 12:
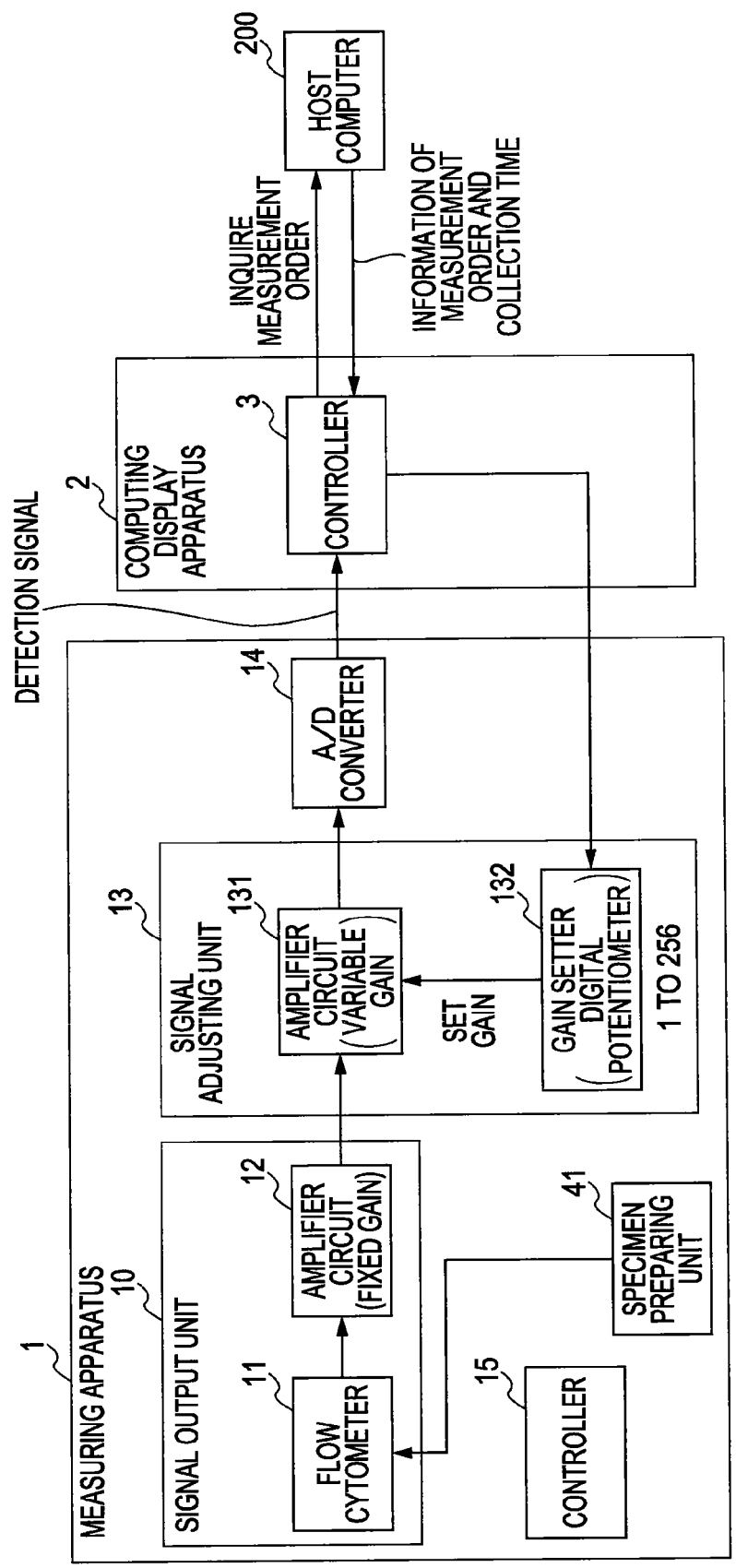
FIG. 12 is a block diagram illustrating another structure of the sample analyzer according to the present embodiment.

FIG. 12 is a block diagram illustrating another structure of the sample analyzer according to the embodiment of the present invention. As illustrated in FIG. 12, for example, a host computer 200 for managing sample-related information is connected to the computing display apparatus 2 in a data communicatable manner in addition to the sample analyzer, and sample-related measurement order and information of a time point when the sample was collected (sample collection time) are stored in the host computer 200 in advance.

To measure the sample, the computing display apparatus 2 inquires of the host computer 200 for the sample-related measurement order. Replying to the inquiry, the host computer 200 transmits the measurement order and information of the sample collection time to the computing display apparatus 2. The computing display apparatus 2 controls the operation of the measuring apparatus 1 in accordance with the received measurement order to measure the sample, and obtains a time point when the sample was measured (measurement time) and measurement data. The computing display apparatus 2 generates an analysis result of the sample based on the obtained measurement data, and stores the analysis result and also the sample collection time and measurement time in the analysis result storing unit 331.

To update the adjustment value, the computing display apparatus 2 extracts the analysis result of a sample which was measured within a predetermined period of time, for example 24 hours, after the sample collection time as the analysis of the sample meeting a predetermined requirement, and calculates the adjustment value based on the extracted analysis result to update the adjustment value already stored.

When the adjustment value is thus calculated based on the analysis result of such a fresh sample, the adjustment value can favorably retain its reliability.

The measurement time is not particularly limited, and may be a point of time when the sample was collected by the measuring apparatus 1, a point of time when the sample-related measurement order was received, or a point of time when the sample analysis result was produced.

Figure 13:
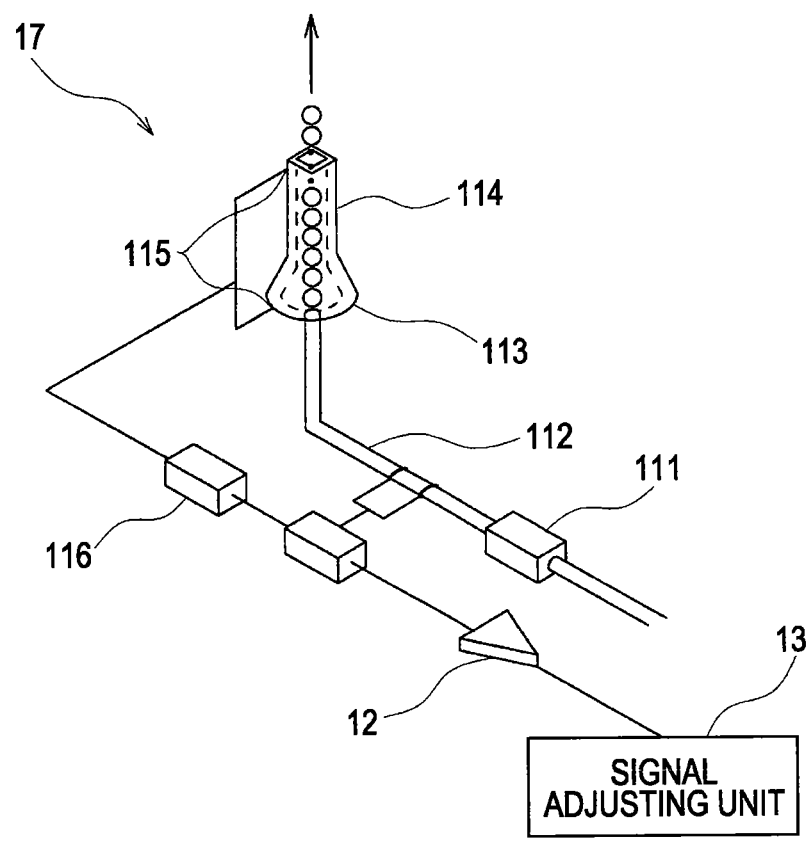
FIG. 13 is a diagram schematically illustrating a structure of an electrical resistance measuring apparatus provided in the sample analyzer according to the preferred embodiment.

The sample analyzer described in the above embodiment uses the optical measuring apparatus 1. However, it is unnecessary that the sample be optically measured by the measuring apparatus 1. For example, the measuring apparatus 1 provided in the sample analyzer may use an electrical resistance instead, preferably exerting a similar effect. FIG. 13 is a diagram schematically illustrating an electrical resistance measuring apparatus 17 of the sample analyzer according to the present embodiment. The electric resistance measuring apparatus 17 outputs a measured electrical signal to the amplifier circuit 12 in place of the flow cytometer 11. In a manner similar to the embodiment described above, the measuring apparatus 17 and the amplifier circuit 12 constitute the signal output section 10.

The electrical resistance measuring apparatus 17 has a reaction unit 111, wherein blood that is a sample is suctioned by a suction tube, and a diluent is introduced into the reaction unit 111.

A flow channel 112 extends from the reaction unit 111, and a sheath flow cell 113 is provided at a terminal end of the flow channel 112. The measurement specimen diluted in the reaction unit 111 is transferred into the sheath flow cell 113 through the flow channel 112. The measurement apparatus 17 is further provided with a sheath liquid chamber which is not illustrated, wherein a sheath liquid stored in the sheath liquid chamber is supplied to the sheath flow cell 113.

In the sheath flow cell 113, the measurement specimen is circulated in such a state that is surrounded by the sheath liquid. The sheath flow cell 113 is provided with an orifice 114, wherein the flow of the measurement specimen is narrowed by the orifice 114 so that particles (cell components) included in the measurement specimen, one each at a time, pass through the orifice 114. A pair of electrodes 115 is attached to the sheath flow cell 113 so that the orifice 114 is interposed therebetween. A direct current power source 116 is connected to the pair of electrodes 115 so that a DC current is supplied to between the pair of electrodes 115. While the DC current from the direct current power source 116 is continuously supplied to the pair of electrodes 115, an impedance between the electrodes can be detected.

An electrical resistance signal indicating variation of the impedance is amplified by the amplifier circuit 12 and transmitted to the signal adjusting section 13. The magnitude of the electrical resistance signal is in proportion to the volume (size) of the particle. When the electrical resistance signal is processed, the particle volume can be obtained.

Thereafter, processing steps similar to those described above are performed. Then, the gain is appropriately set to amplify the electrical resistance signal by using the adjustment value calculated based on the analysis result of the sample meeting a predetermined requirement. Therefore, it is unnecessary to search the analysis result of a sample having a certain characteristic in a huge volume of analysis results. When the gain is simply adjusted in such a manner that flexibly respond to the circumstances of a site where the sample analyzer is used, the detection sensitivity of the electrical resistance measuring apparatus 17 can be suitably adjusted. As a result, a more appropriate output signal can be obtained.

The present invention is not necessarily limited to the embodiments described above, and can be variously modified and replaced with other modes as far as they stay within the scope of technical significance of the present invention. For example, the output signal is not necessarily simply amplified to adjust the gain as described above. The output signal can be gradually amplified through stages, or uniform shift up of the output voltage is another option.

What is claimed is:

1. A sample analyzer for analyzing particles contained in a sample comprising:
    a measuring unit, which comprises a specimen preparing unit for preparing a first measurement specimen by mixing a portion of a sample with a first reagent and preparing a second measurement specimen by mixing a portion of the sample with a second reagent, a signal output section for outputting a signal representing a characteristic of particles in each measurement specimen, and a signal adjusting section for adjusting the signal outputted from the signal output section, the measuring unit outputting a measurement data based on the signal adjusted by the signal adjusting section;
    a result producing unit including a storage device for storing a plurality of analysis results of a plurality of samples, the result producing unit producing a first analysis result by analyzing a first group of particles based on a first measurement data obtained from the first measurement specimen and producing a second analysis result by analyzing a second group of particles based on a second measurement data obtained from the second measurement specimen, and storing the first analysis result and the second analysis result in the storage device, wherein
    the result producing unit:
        determines whether predetermined numbers of first analysis results of samples, each included in a predetermined numerical range, have been stored in the storage device;
        in response to the determination that the predetermined numbers of first analysis results have been stored in the storage device,
        reads out, from the storage device, the predetermined numbers of second analysis results of the samples whose first analysis results are included in the predetermined numerical range;
        calculates an adjustment value, which is to be used in the signal adjustment by the signal adjusting section, based on the predetermined numbers of second analysis results read out from the storage device; and
        transmits the calculated adjustment value to the measuring unit for use in a measurement of subsequent samples, and
    the signal adjusting section adjusts a signal of particles in the subsequent samples outputted from the signal output section based on the adjustment value transmitted from the result producing unit.

2. The sample analyzer of claim 1, wherein
the signal output section comprises:
    a light source for radiating light on each of the first and second measurement specimens; and
    a light receiver for receiving light generated from each of the first and second measurement specimens and outputting a signal corresponding to a volume of the received light.

3. The sample analyzer of claim 1, wherein
the signal adjusting section amplifies the signal outputted from the signal output section based on the adjustment value.

4. The sample analyzer of claim 1, wherein
the result producing unit:
    receives an update command which commands to update the adjustment value;
    reads out second analysis results of samples whose first analysis results are included in the predetermined numerical range when the update command is received; and
    calculates the adjustment value based on the read out second analysis results.

5. The sample analyzer of claim 1, wherein
the result producing unit, when a first analysis result of a sample meeting the predetermined numerical range is newly produced and stored in the storage device, determines whether the predetermined numbers of first analysis results, each included in the predetermined numerical range, have been stored in the storage device.

6. The sample analyzer of claim 1, wherein
the result producing unit reads out second analysis results of samples each of which were measured by the measuring unit within a predetermined period of time after respective sample had been collected.

7. The sample analyzer of claim 1, wherein the signal adjusting section comprises:
   a gain setter for setting a gain based on the adjustment value transmitted from the result producing unit; and
   an amplifier for amplifying the signal outputted from the signal output section based on the gain set by the gain setter.

8. The sample analyzer of claim 7, wherein the measuring unit further comprises an A/D converter which converts the signal amplified by the amplifier into a digital signal, and
   the measuring unit outputs the digital signal as the measurement data.

9. The sample analyzer of claim 1, wherein the result producing unit calculates the adjustment value based on numeral values included in the read out second analysis results and a predetermined target value.

10. The sample analyzer of claim 1, wherein
    the signal output section outputs a first characteristic signal representing a first characteristic of each measurement specimen and a second characteristic signal representing a second characteristic of each measurement specimen,
    the result producing unit calculates a first adjustment value used in the adjustment of the first characteristic signal by the signal adjusting section and a second adjustment value used in the adjustment of the second characteristic signal by the signal adjusting section based on the read out second analysis results, and transmits the calculated first and second adjustment values to the measuring unit, and
    the signal adjustment section adjusts the first characteristic signal based on the received first adjustment value, and adjusts the second characteristic signal based on the received second adjustment value.

11. The sample analyzer of claim 1, wherein
    the result producing unit comprises a memory for storing therein the calculated adjustment value, and
    when the adjustment value is calculated, the result producing unit stores the calculated adjustment value in the memory, and when a command to measure the sample is received, the result producing unit transmits the stored adjustment value to the measuring unit.

12. The sample analyzer of claim 11, wherein
    the memory stores therein a plurality of adjustment values which are linked to measurement items, and
    the result producing unit reads out the adjustment value, corresponding to the measurement item commanded to be measured, from the memory and transmits the read adjustment value to the measuring unit.

13. The sample analyzer of claim 1, wherein
    the result producing unit stores an analysis result in the storage device every time a new analysis result is produced.

14. The sample analyzer of claim 1, wherein
    the second group of particles are white blood cells,
    the result producing unit produces the second analysis result by classifying the white blood cells in the second measurement specimen into clusters and generating a distribution data indicating a position of each of the clusters,
    the result producing unit calculates, for each of the predetermined numbers of second analysis results read out from the storage device, a difference between a value reflecting the position of the classified cluster and a value reflecting a target position in the distribution data, and
    calculates the adjustment value based on the differences calculated from the predetermined numbers of second analysis results.

15. A non-transitory computer readable medium encoded with a computer program product for a sample analyzer, the sample analyzer comprising:
    a measuring unit, which comprises a specimen preparing unit for preparing a first measurement specimen by mixing a portion of a sample with a first reagent and preparing a second measurement specimen by mixing a portion of the sample with a second reagent, a signal output section for outputting a signal representing a characteristic of particles in each measurement specimen, and a signal adjusting section for adjusting the signal outputted from the signal output section, the measuring unit configured to output a measurement data based on the signal adjusted by the signal adjusting section; and
    a result producing unit including a storage device for storing a plurality of analysis results of a plurality of samples, the result producing unit producing a first analysis result by analyzing a first group of particles based on a first measurement data obtained from the first measurement specimen and producing a second analysis result by analyzing a second group of particles based on a second measurement data obtained from the second measurement specimen, and storing the first analysis result and the second analysis result in the storage device, wherein
    the computer program includes instructions adapted to enable the result producing unit to carry out operations, comprising:
    determining whether predetermined numbers of first analysis results of samples, each included in a predetermined numerical range, have been stored in the storage device;
    in response to the determination that the predetermined numbers of first analysis results have been stored in the storage device,
    reading out, from the storage device, the predetermined numbers of second analysis results of the samples whose first analysis results are included in the predetermined numerical range;
    calculating an adjustment value used in the signal adjustment by the signal adjusting section based on the predetermined numbers of second analysis results read out from the storage device; and
    transmitting the calculated adjustment value to the measuring unit for use in a measurement of subsequent samples.

* * * * *